United States Patent
Kobayashi et al.

(10) Patent No.: US 7,413,554 B2
(45) Date of Patent: Aug. 19, 2008

(54) WEARABLE JOINT DRIVING DEVICE

(75) Inventors: Hiroshi Kobayashi, Chiba (JP); Yutaka Sato, Chiba (JP); Kazuaki Hiramatsu, Ibaraki (JP); Makoto Konami, Chiba (JP); Taisuke Matsushita, Chiba (JP); Masaaki Muromachi, Saitama (JP); Akitaka Uchimura, Tokyo (JP)

(73) Assignees: Hitachi Medical Corporation, Tokyo (JP); Tokyo University of Science, Shinjuku-Ku (JP)

( * ) Notice: Subject to any disclaimer, the term of this patent is extended or adjusted under 35 U.S.C. 154(b) by 80 days.

(21) Appl. No.: 10/543,403

(22) PCT Filed: Mar. 18, 2004

(86) PCT No.: PCT/JP2004/003635

§ 371 (c)(1),
(2), (4) Date: Jul. 26, 2005

(87) PCT Pub. No.: WO2004/087033

PCT Pub. Date: Oct. 14, 2004

(65) Prior Publication Data

US 2006/0161220 A1  Jul. 20, 2006

(30) Foreign Application Priority Data

Mar. 28, 2003 (JP) ............................. 2003-091280

(51) Int. Cl.
*A61F 5/00* (2006.01)

(52) U.S. Cl. .............................. 602/19; 602/13; 602/32
(58) Field of Classification Search .................. 602/5, 602/13, 19, 32; 601/5; 128/DIG. 20
See application file for complete search history.

(56) References Cited

U.S. PATENT DOCUMENTS

| | | | | |
|---|---|---|---|---|
| 4,531,516 A | * | 7/1985 | Poole et al. | .................... 602/13 |
| 5,391,141 A | * | 2/1995 | Hamilton | ..................... 601/151 |
| 5,423,333 A | * | 6/1995 | Jensen et al. | ................. 128/878 |
| RE36,869 E | * | 9/2000 | Ewen | ............................. 450/1 |

FOREIGN PATENT DOCUMENTS

| | | |
|---|---|---|
| JP | 9-271496 | 10/1997 |
| JP | 2002-103270 | 4/2002 |
| JP | 2002-306282 | 10/2002 |
| JP | 2003-301807 | 10/2003 |

* cited by examiner

*Primary Examiner*—Michael A. Brown
(74) *Attorney, Agent, or Firm*—Antonelli, Terry, Stout & Kraus, LLP.

(57) ABSTRACT

Provided is a wearable joint driving device in which a plurality of frame members are attached to a wearing body so as to be in contact with the outer surface of the wearing body. Between the frame members, there is mounted a fluid pressure type actuator. The fluid pressure type actuator has an expansion/contraction member and a net-like covering member covering the outer periphery of the expansion/contraction member. The fluid pressure type actuator undergoes a reduction in length through expansion of the expansion/contraction member to thereby generate a driving force. The frame members have a predetermined level of rigidity.

16 Claims, 12 Drawing Sheets

WEARABLE JOINT DRIVING DEVICE

TECHNICAL FIELD

The present invention relates to a wearable joint driving device worn by a human body or the like to allow a joint portion to make a movement.

BACKGROUND ART

JP 2002-103270 A discloses a wearable joint driving device worn by a human body to allow a joint portion to make a movement. In the conventional wearable joint driving device, a plurality of pneumatic actuators, which are reduced in length through air supply to generate a driving force, are mounted to clothes worn by the human body. That is, in the above-mentioned device, by reducing the length of the pneumatic actuators, a contraction force is exerted between link bodies formed in the clothes, thereby driving joint portions of the human body.

However, in the above conventional wearable joint driving device, a force from the pneumatic actuators acts on the link bodies of the clothes formed of a flexible material such as cloth, so that wrinkles, looseness, or the like may be generated in the clothes, and the clothes may be deviated with respect to the human body. Accordingly, there is a fear of the operating amount of the pneumatic actuators not being properly transmitted to the human body, making it impossible to obtain a sufficient operating amount and driving force for practical use.

DISCLOSURE OF THE INVENTION

The present invention has been made with a view toward solving the above problem. It is an object of the present invention to provide a wearable joint driving device capable of achieving an improvement in driving force transmission efficiency and an increase in operating amount and driving force.

To this end, according to one aspect of the present invention, there is provided a wearable joint driving device worn by a driven body having a plurality of wearing members and at least one joint portion rotatably connecting the wearing members to drive the joint portion, the wearable joint driving device comprising: a plurality of frame members of a predetermined rigidity to be attached to the wearing members so as to be in contact with outer surfaces of the wearing members; at least one fluid pressure type actuator having an expansion/contraction member undergoing expansion/contraction through supply/discharge of a fluid and a net-like covering member covering an outer periphery of the expansion/contraction member, and mounted between the frame members, the expansion/contraction member being reduced in length through expansion to thereby generate a driving force; and a control unit for controlling supply and discharge of the fluid to and from the fluid pressure type actuator.

According to another aspect of the present invention, there is provided a wearable joint driving device worn by a driven body having first and second wearing members and a joint portion rotatably connecting the first and second wearing members to drive the joint portion, the wearable joint driving device comprising: a first frame member to be attached to the first wearing member; a second frame member to be attached to the second wearing member; a rotation support member rotatably connected to the first frame member; a second frame member actuator provided between at least one of the first frame member and the rotation support member and the second frame member and adapted to rotate the second frame member with respect to the first frame member; and a support member actuator provided between the first frame member and the rotation support member and adapted to rotate the rotation support member with respect to the first frame member, wherein the second frame member actuator and the support member actuator are fluid pressure type actuators respectively having an expansion/contraction member undergoing expansion/contraction through supply/discharge of a fluid and a net-like covering member covering an outer periphery of the expansion/contraction member, the expansion/contraction member being reduced in length through expansion to generate a driving force, wherein the second frame member is rotated from a first position to a second position with respect to the first frame member by the driving force of the second frame member actuator, and wherein, by driving the support member actuator with the second frame member being at the second position, the second frame member is rotated together with the rotation support member, whereby the second frame member is rotated to a third position where the angle the second frame member makes with the first position is larger than that when the second frame member is at the second position.

BRIEF DESCRIPTION OF THE DRAWINGS

FIG. 7b is a sectional view taken along the line A-A of FIG. 7a;

FIG. 8 is a block diagram showing the wearable joint driving device of FIG. 7a;

BEST MODE FOR CARRYING OUT THE INVENTION

In the following, preferred embodiments of the present invention will be described with reference to the drawings.

Embodiment 1

Figure 1:
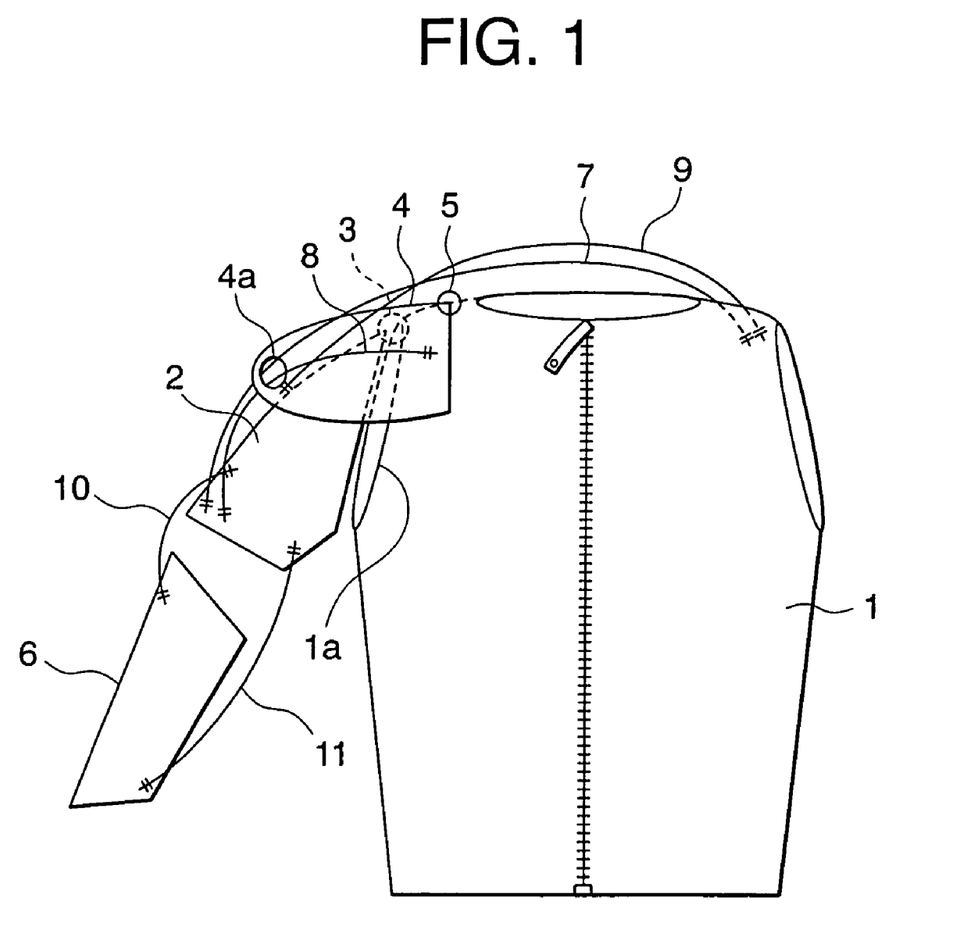
FIG. 1 is a front view of a wearable joint driving device according to Embodiment 1 of the present invention.

FIG. 1 is a front view of a wearable joint driving device according to Embodiment 1 of the present invention. In this example, the device shown is of a type which is worn by the upper part of a human body and which drives a shoulder joint portion and an elbow joint portion of one arm. Further, in this example, what is driven is a part of a human body. The torso (body) constitutes a first wearing body, the upper arm constitutes a second wearing body, and the forearm constitutes a third wearing body. The body and the upper arm are connected by the shoulder joint portion, and the upper arm and the forearm are connected by the elbow joint portion.

In the drawing, a torso frame 1 as a first frame member is put on the torso. The torso frame 1 is provided with a sleeve opening 1a through which the arm is to be passed. Further, inside the torso frame 1, there is provided a fixation belt (not shown) for preventing movement of the torso frame 1 relative to the torso.

An upper arm frame 2 as a second frame member is put on the upper arm. That is, the upper arm is passed through the cylindrical upper arm frame 2. The upper arm frame 2 is rotatably connected to the torso frame 1 at a connecting portion 3. A shoulder frame 4 as a rotation support member is rotatably connected to the torso frame 1 through the intermediation of a connecting portion 5. The connecting portions 3, 5 are spaced apart from each other. That is, the positions of the respective rotation centers of the upper arm frame 2 and the shoulder frame 4 are deviated from each other.

A forearm frame 6 is put on the forearm. That is, the forearm is passed through the cylindrical forearm frame 6. The torso frame 1, the upper arm frame 2, and the forearm frame 6 are attached so as to be respectively brought into contact with the outer surfaces of the torso, the upper arm, and the forearm. Further, the torso frame 1, the upper arm frame 2, the shoulder frame 4, and the forearm frame 6 have a predetermined level of rigidity that allows the same operation irrespective of whether they are on the human body or not. More specifically, the frames 1, 2, 4, 6 are formed by non-metal soft frames consisting of hard resin or sponge covered with cloth.

Between the torso frame 1 and the upper arm frame 2, there is provided a tubular first actuator 7 as the second frame member actuator for rotating the upper arm frame 2 relative to the torso frame 1. The end portions of the first actuator 7 are respectively fixed to the other shoulder portion of the torso frame 1 and the portion of the upper arm frame 2 in the vicinity of the elbow joint.

Between the shoulder frame 4 and the upper arm frame 2, there is provided a tubular second actuator 8 as the second frame member actuator for attracting the upper arm frame 2 to the shoulder frame 4. The end portions of the second actuator 8 are respectively fixed to the portion of the shoulder frame 4 in the vicinity of the shoulder portion and the portion of the upper arm frame 2 in the vicinity of the elbow joint. The shoulder frame 4 is provided with a guide portion (guide hole) 4a through which the first and second actuators 7, 8 are passed.

Between the torso frame 1 and the shoulder frame 4, there is provided a tubular third actuator 9 as the auxiliary member actuator for rotating the shoulder frame 4 relative to the torso frame 1. The end portions of the third actuator 9 are fixed to the other shoulder portion of the torso frame 1 and the portion of the shoulder frame 4 in the vicinity of the forward end thereof.

Between the upper arm frame 2 and the forearm frame 6, there are provided tubular fourth and fifth actuators 10, 11 for rotating the forearm 6 relative to the upper arm frame 2. The end portions of the fourth and fifth actuators 10, 11 are respectively fixed to the portion of the upper arm frame 2 in the vicinity of the elbow joint, the portion of the forearm frame 6 in the vicinity of the elbow joint, and the portion of the forearm frame 6 in the vicinity of the forward end thereof.

While it is possible to attach, apart from the above-mentioned ones, a plurality of other actuators to the frames 1, 2, 4, 6 according to the directions in which the joint portions are to be moved and the requisite driving forces, only the first through fifth actuators 7 through 11 are shown here for the sake of simplicity.

Figure 2:
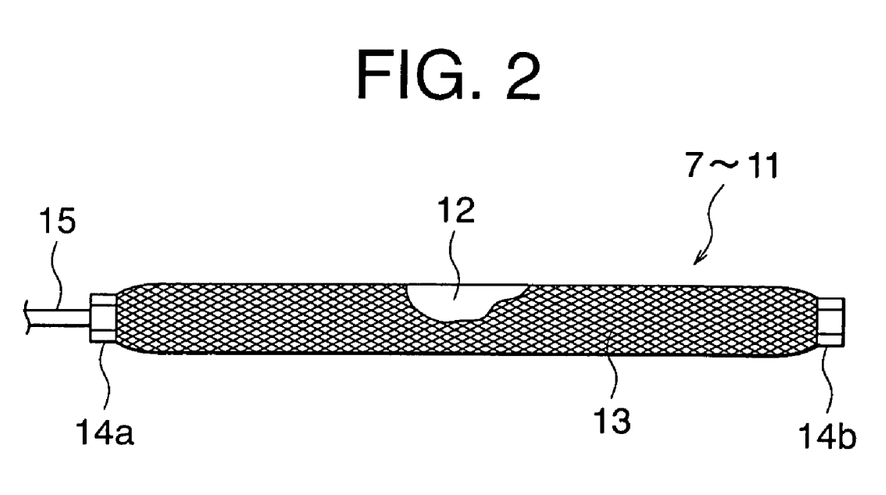
FIG. 2 is a side view of an actuator of FIG. 1.
Figure 3:
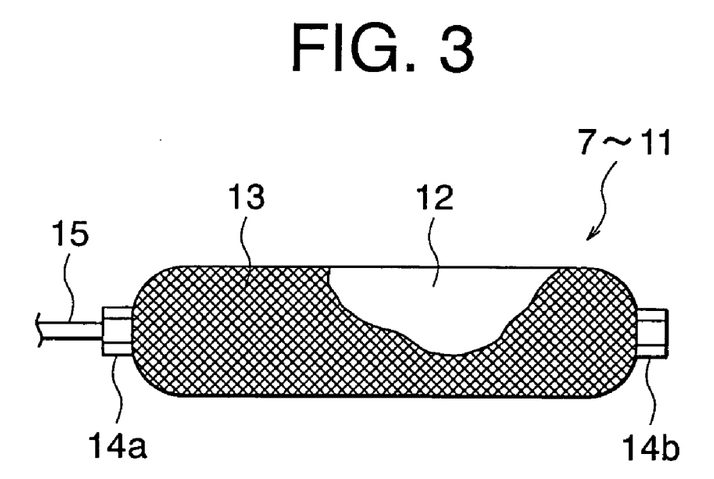
FIG. 3 is a side view of the actuator of FIG. 1 in a swollen state.

FIG. 2 is a side view of each of the actuators 7 through 11 of FIG. 1, and FIG. 3 is a side view of each of the actuators 7 through 11 of FIG. 1 in a swollen state. While in FIG. 1 the first through fifth actuators 7 through 11 are shown simply as curves, each of the actuators 7 through 11 has a construction as shown in FIGS. 2 and 3. Further, in FIGS. 2 and 3, part of the mesh sleeve is cut away in order to show the internal structure.

In the drawings, as the first through fifth actuators 7 through 11, pneumatic actuators, which are fluid pressure type actuators, are used. Connected to one end in the longitudinal direction of an inner tube 12 as an expansion/contraction body is a supply/discharge pipe 15 for supplying and discharging air serving as the fluid to and from the inner tube 12. A bush (not shown) is inserted into the other longitudinal end portion of the inner tube 12 for hermetic sealing. The inner tube 12 is formed of an elastic material such as silicone rubber or butyl rubber.

The outer periphery of the inner tube 12 is covered with a mesh sleeve 13, which is a net-like covering member. The mesh sleeve 13 is formed, for example, of filaments (wires) of high tensile fibers or the like such as nylon or polyester fiber that has no elasticity. In the meshes of the mesh sleeve 13, the fibers are woven so as to cross the longitudinal direction of the mesh sleeve 13. The longitudinal end portions of the mesh sleeve 13 are fastened by fastening members 14a, 14b, whereby they are fixed to the end portions of the inner tube 12.

The inner tube 12 expands when air is supplied into it. Since the filaments forming the mesh sleeve 13 have no elasticity, the expansion of the inner tube 12 is converted to a reduction in the total length of the actuator. That is, when supplied with air, the length of each of the actuators 7 through 11 is reduced while its diameter increases. Due to this reduction in length, the actuators 7 through 11 generates driving force (pulling force).

Figure 4:
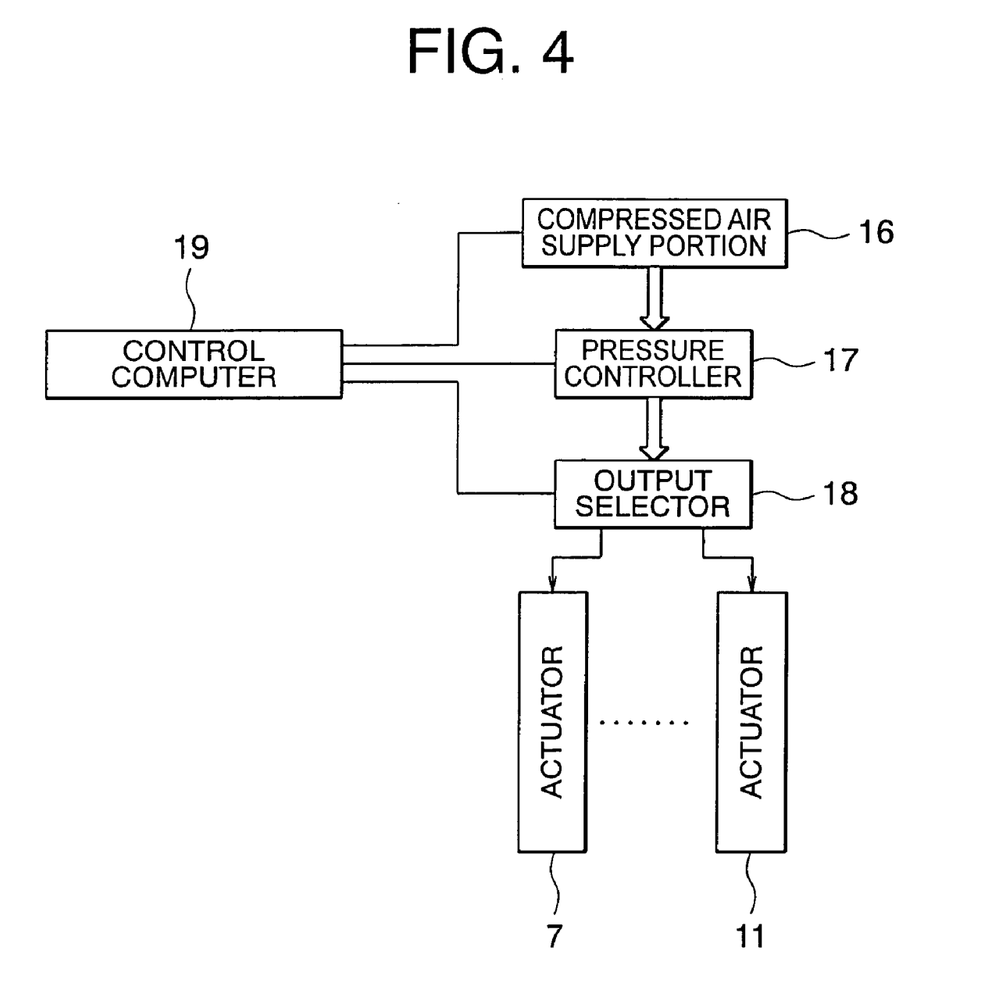
FIG. 4 is a block diagram showing the wearable joint driving device of FIG. 1.

Next, FIG. 4 is a block diagram showing the construction of the drive control portion of the wearable joint driving device of FIG. 1. The actuators 7 through 11 are supplied with air from a compressed air supply portion 16 consisting, for example, of a small air compressor. The pressure of the air supplied from the compressed air supply portion 16 to the actuators 7 through 11 is adjusted by one or a plurality of pressure controllers 17. Further, the supply of air to the actuators 7 through 11 is effected selectively or in parallel by an output selector 18. The compressed air supply portion 16, the pressure controller 17, and the output selector 18 are controlled by a control computer 19. A control unit has the pressure controller 17 and the output selector 18.

Figure 5:
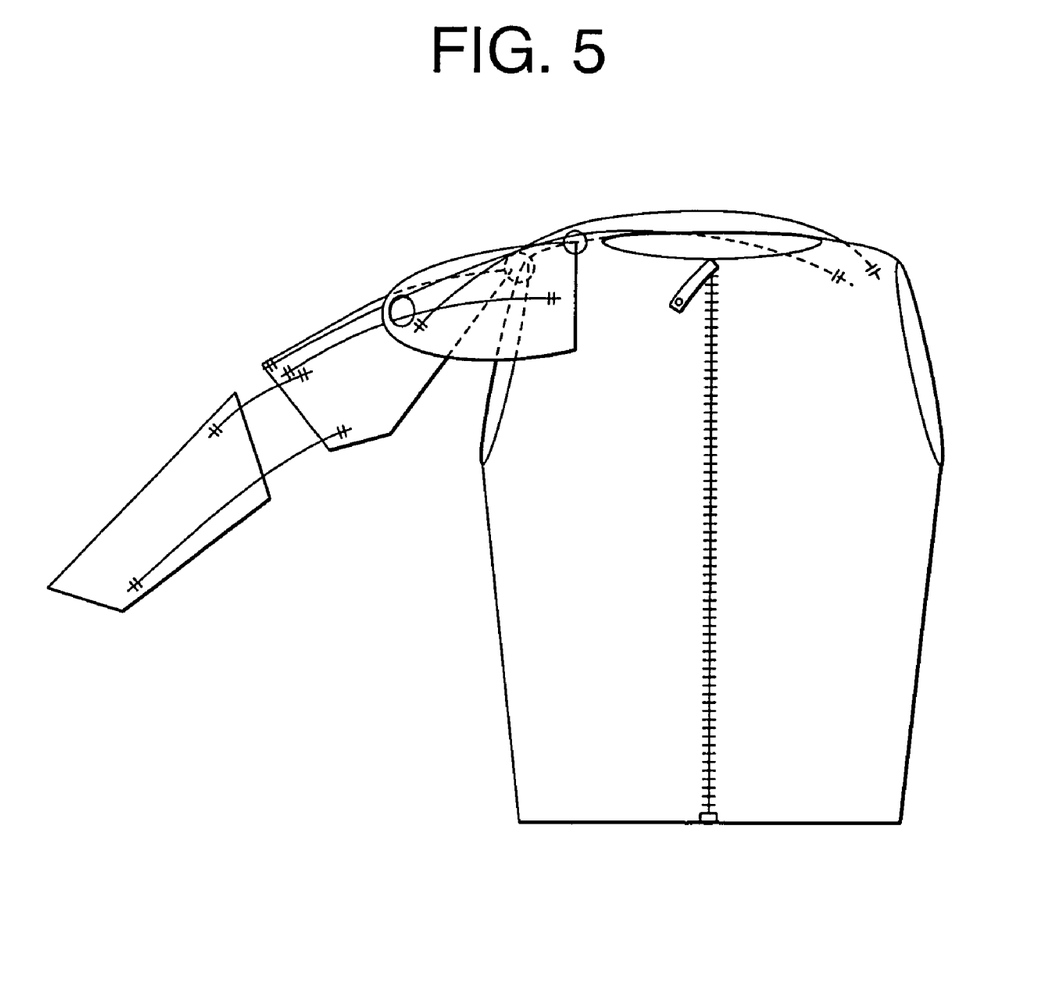
FIG. 5 is a front view showing an upper arm frame of FIG. 1 as rotated to a second position.
Figure 6:
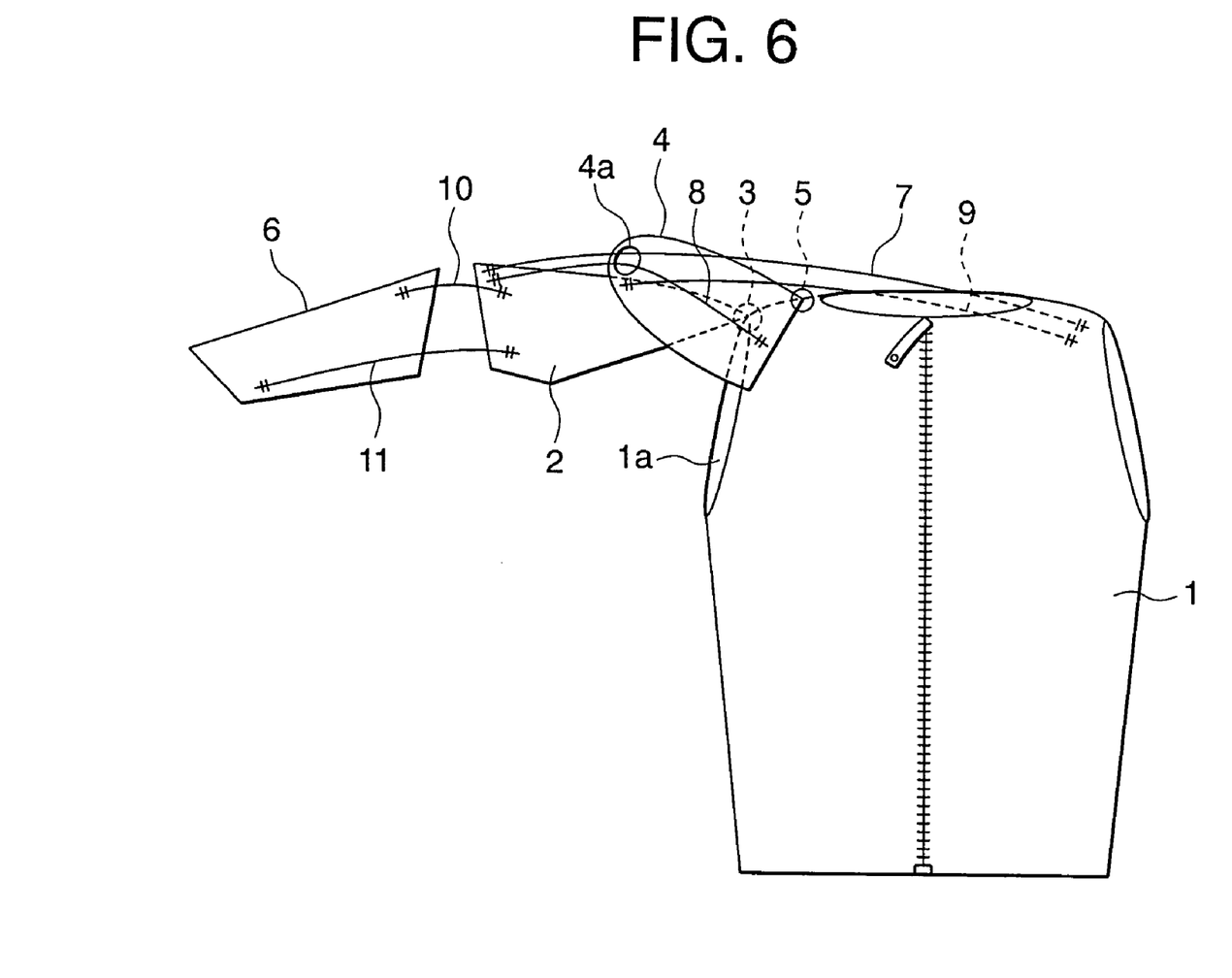
FIG. 6 is a front view showing the upper arm frame of FIG. 5 as rotated to a third position.

Next, the operation of the device will be described. By supplying air to the first and second actuators 7, 8, the first and second actuators 7, 8 are reduced in length, and as shown in FIG. 5, the upper arm frame 2 is raised. When, in this state, air is supplied to the third actuator 9, the upper arm frame 2 is further raised together with the shoulder frame 4 as shown in FIG. 6.

That is, the upper arm frame 2 is rotated from a first position (FIG. 1) to a second position (FIG. 5) relative to the torso frame 1 by the driving force of the first and second actuators 7, 8. Then, by driving the third actuator 9, with the upper arm frame 2 being at the second position (FIG. 5), the upper arm frame 2 is rotated together with the shoulder frame 4. As a result, the upper arm frame 2 is rotated to a third position (FIG. 6) where the angle it makes with the first position (FIG. 1) is larger than that when it is at the second position (FIG. 5).

In the wearable joint driving device described above, the torso frame 1, the upper arm frame 2, the shoulder frame 4, and the forearm frame 6 have a predetermined level of rigidity which, even if they are not on the human body, allows them to operate in the same manner as when they are on the human body, so that generation of wrinkles and looseness in the frames 1, 2, 4, 6 is prevented, making it possible to achieve an improvement in terms of driving force transmission efficiency and to achieve an increase in operating amount and driving force.

That is, the frames 1, 2, 4, 6 also function as armor-like frames like the outer skeleton of a crustacean, such as an insect. Regarding the combination and arrangement of the frames, it is desirable to adopt, taking into account the actual arrangement of bones, joint portions, and muscles of the human, ones in which there is no local excessive load on the skin, bones, and joints in various limb portions, making the rotation centers of the joint portions as the same as or equivalent to those for the movements of the human body.

Further, due to the use of the shoulder frame 4 and the third actuator 9 for rotating the shoulder frame 4, it is possible to extend the rotation range for the upper arm frame 2. That is, with the first actuator 7 alone, it is only possible to outwardly rotate the upper arm frame 2 by approximately 70 degrees, whereas, by rotating the upper arm frame 2 together with the shoulder frame 4 by means of the third actuator 9, outward rotation by 90 degrees or more is possible.

By thus adding the shoulder frame 4 and the third actuator 9, the shoulder and the peripheral joint portion have ceased to be treated as a joint with only one rotation axis, making it possible to realize an operation equivalent to that of the human body, in which the rotation center undergoes transition according to the operation.

Further, inside the torso frame 1, there is provided a belt for fixing the torso frame 1 to the human body, so that absorption of the driving force of the actuators 7 through 11 by the movement of the torso frame 1 is prevented, making it possible to achieve a further improvement in driving force transmission efficiency. Further, the force from the actuators 7 through 11 is received by the torso frame 1, and not by the belt, so that no load from the belt is applied to the wearing person.

While in the above example the shoulder frame 4 and the third actuator 9 are used in order to expand the rotation range for the upper arm frame 2, it is also possible to use a rotation support member and an auxiliary member actuator for expanding the rotation range for another frame member.

Further, while the example shown above consists of a wearable joint driving device for driving one arm, it is also possible to put the device on some other portion of the human body to drive some other joint portion.

Embodiment 2

Figure 7A:
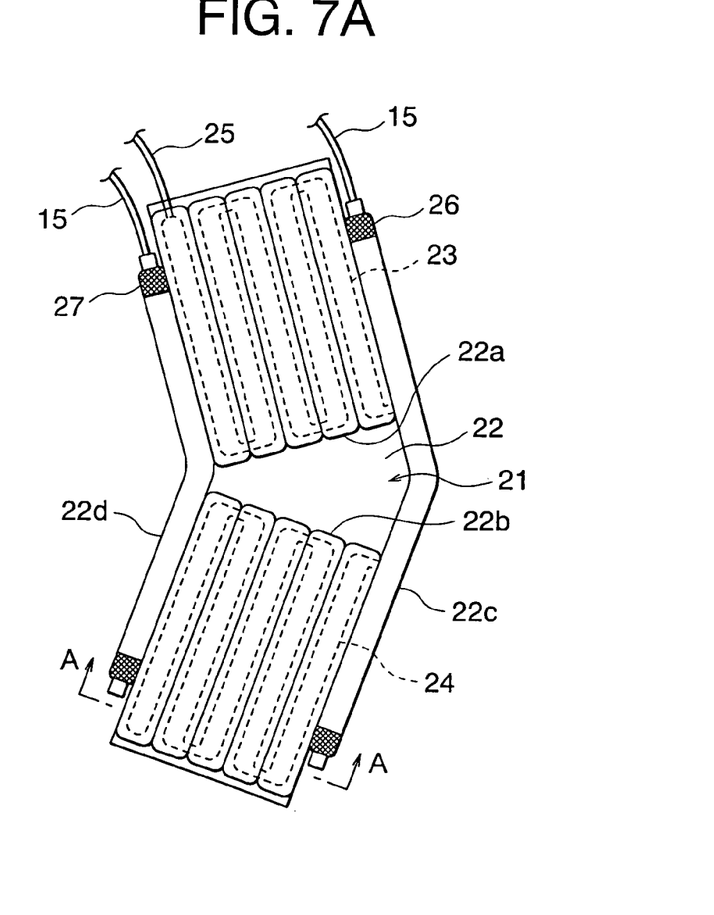
FIG. 7a is a side view of a wearable joint driving device according to Embodiment 2 of the present invention.
Figure 7B:
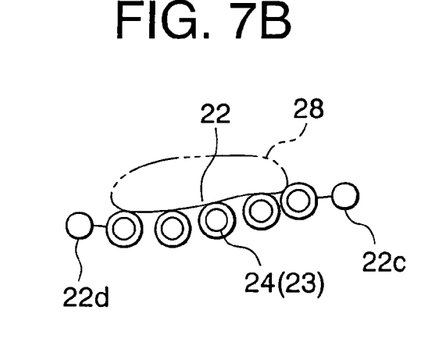
Figure 7C:
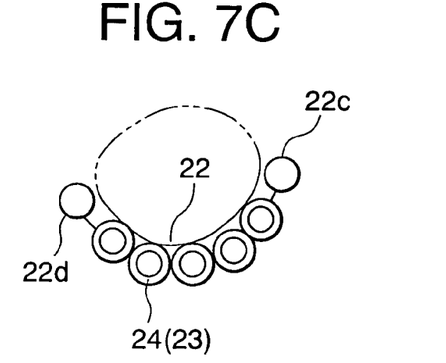
FIG. 7c is a sectional view showing a state in which air has been supplied to a frame tube of FIG. 7b.
Figure 8:
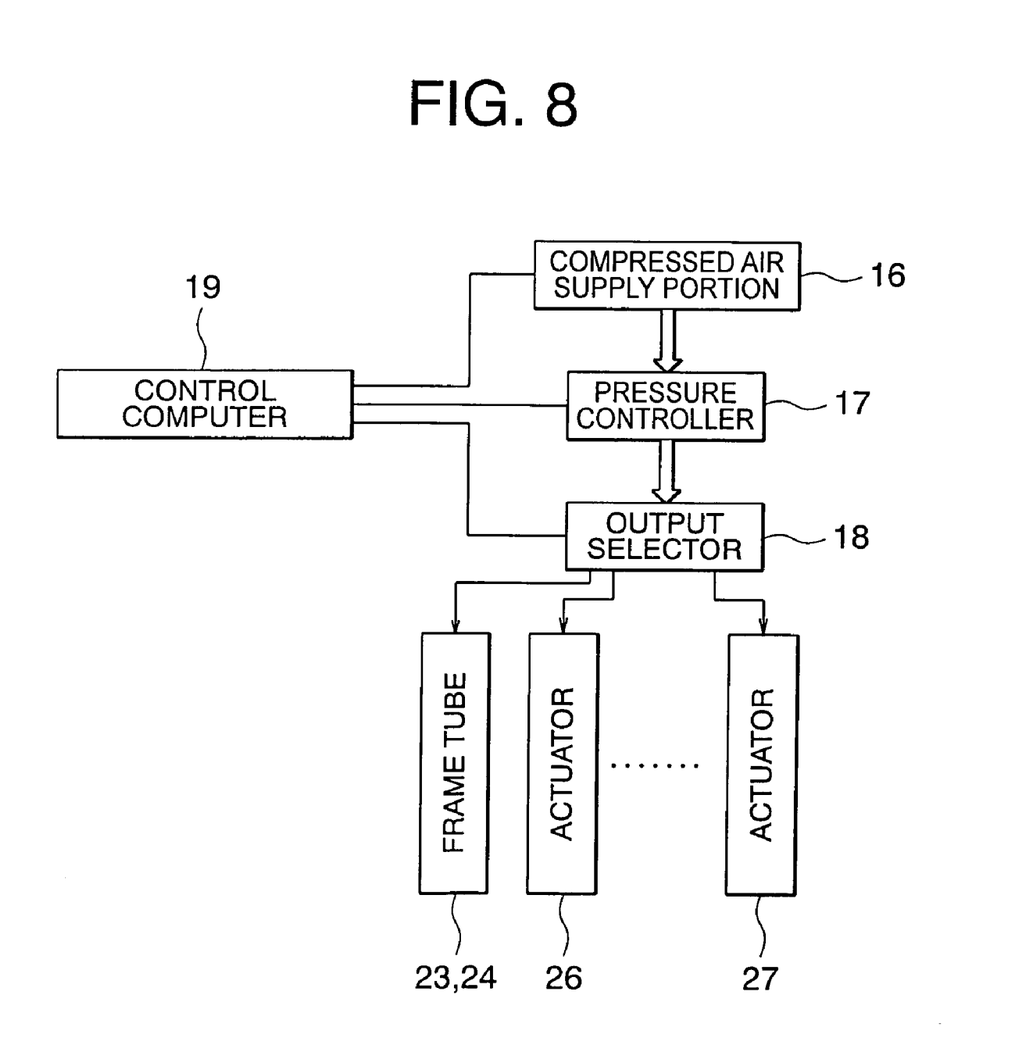

Next, FIG. 7*a* is a side view of a wearable joint driving device according to Embodiment 2 of the present invention, FIG. 7*b* is a sectional view taken along the line A-A of FIG. 7*a*, FIG. 7*c* is a sectional view showing a state in which air has been supplied to the frame tube of FIG. 7*b*, and FIG. 8 is a block diagram showing the construction of the operation control portion of the wearable joint driving device of FIG. 7*a*. In this example, the device shown is of the type which is put on a knee portion of the human body to cause the knee joint to make bending and stretching motions. Further, a thigh portion and a lower leg portion, to which this device is put on, are rotatably connected at the knee portion constituting the joint portion.

In the drawings, a frame member 21 has a support member 22 on which the thigh portion and the lower leg portion are placed, and first and second frame tubes 23, 24 contained in the support member 22. Air is supplied to the first and second frame tubes 23, 24 through a supply/discharge tube 25. By supplying air to the frame tubes 23, 24, the frame member 21 attains a predetermined level of rigidity, and the frame member 21 is flexible with the air discharged therefrom.

The support member 22 has a first accommodating portion 22*a* accommodating the first frame tubes 23, a second accommodating portion 22*b* accommodating the second frame tubes 24, a first actuator inserting portion 22*c*, and a second actuator inserting portion 22*d*. As shown in section in FIG. 7*b*, the first accommodating portion 22*a* and the second accommodating portion 22*b* are formed such that the top portions of the tubes arranged in parallel are connected to each other.

A first actuator 26 is inserted into the first actuator inserting portion 22*c*. The end portions of the first actuator 26 are fixed to the support member 22. A second actuator 27 is inserted into the second actuator inserting portion 22*d*. The end portions of the second actuator 27 are fixed to the support member 22. The construction of the first and second actuators 26, 27 is the same as that shown in FIGS. 2 and 3.

In the wearable joint driving device described above, by supplying air to the first and second frame tubes 23, 24, the first and second accommodating portions 22*a*, 22*b* are formed into a concave configuration as shown in FIG. 7*c*, wrapping the thigh portion and the lower leg portion placed thereon. Then, by supplying and discharging air to and from the first and second actuators 26, 27, a pulling force is exerted on the frame member 21, allowing the knee joint to bend and stretch. At this time, due to the supply of air to the frame tubes 23, 24, the frame member 21 attains a predetermined level of rigidity (a level of rigidity allowing the same operation irrespective of whether it is on the human body or not), so that it is possible to achieve an improvement in terms of driving force transmission efficiency, making it possible to increase the operating amount and the driving force. Further, with air discharge therefrom, the frame member 21 is flexible, so that it is possible to achieve an improvement in terms of comfort during use. Further, when the device is not in use, its accommodation and transportation can be facilitated. Further, it is possible to achieve a reduction in the weight of the device as a whole, and an improvement in terms of comfort when the device on the human body.

As indicated by the chain line in FIG. 7*b*, in this embodiment, the support member 22 may form on the front side or the back side of the frame tubes 23, 24 a bag-like member 28 into which the arm or the leg is to be inserted.

Embodiment 3

Figure 9:
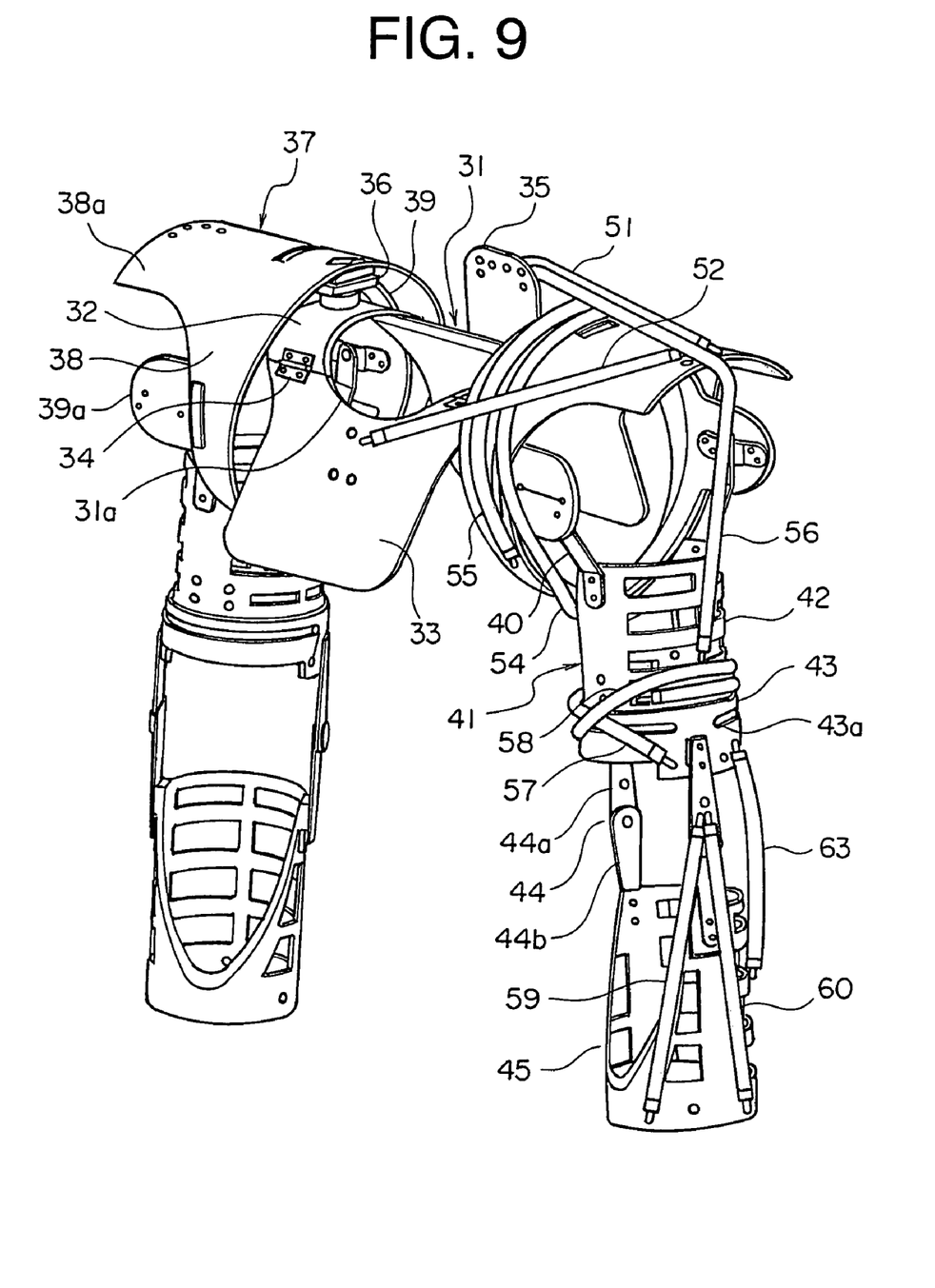
FIG. 9 is a perspective view, as seen obliquely from the front right-hand side, of a wearable joint driving device according to Embodiment 3 of the present invention.
Figure 10:
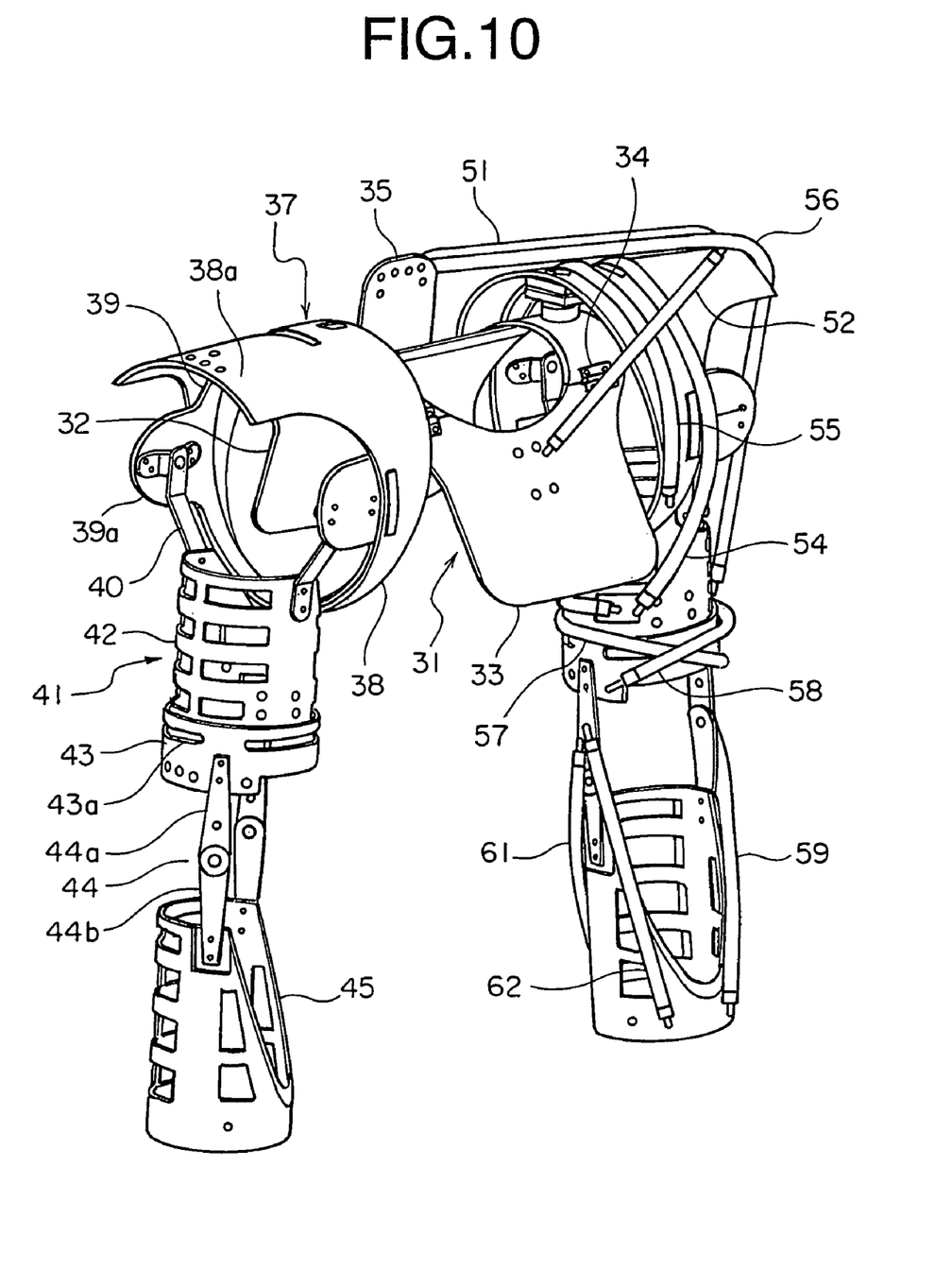
FIG. 10 is a perspective view, as seen obliquely from the front left-hand side, of the wearable joint driving device of FIG. 9.
Figure 11:
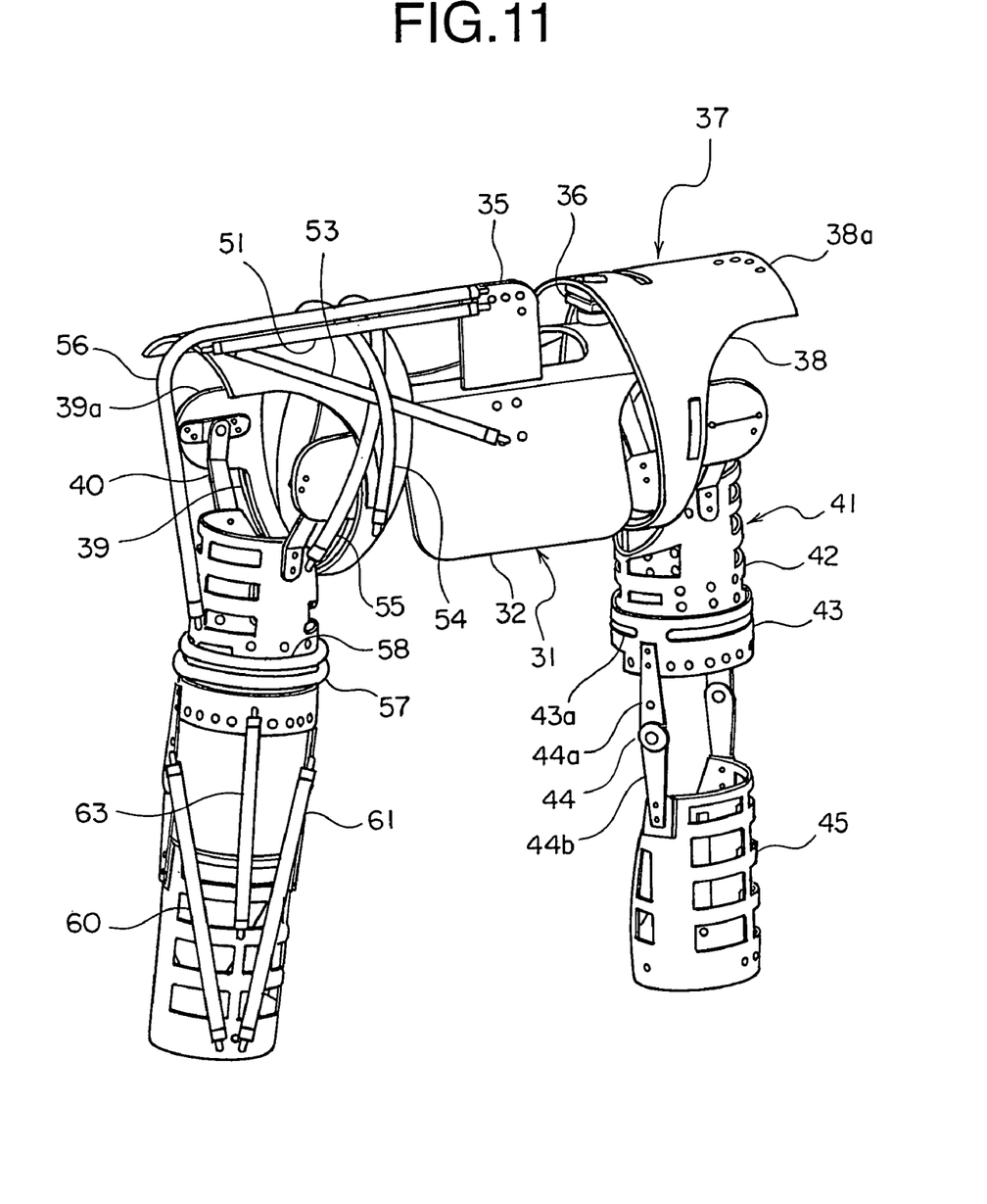
FIG. 11 is a perspective view, as seen obliquely from the rear left-hand side, of the wearable joint driving device of FIG. 9.
Figure 12:
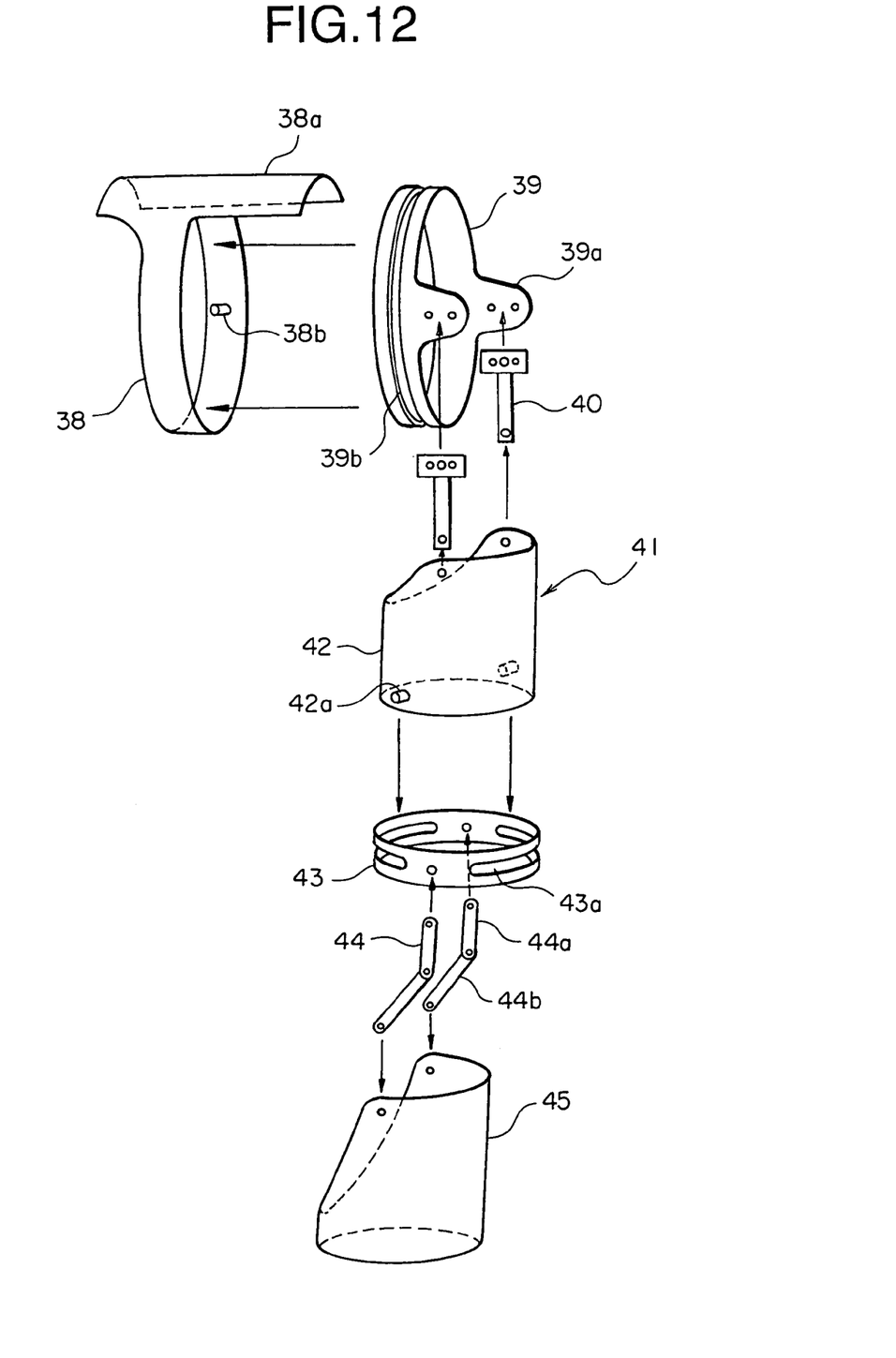
FIG. 12 is an exploded perspective view showing the left-arm side frame construction of the wearable joint driving device of FIG. 9.

Next, FIG. 9 is a perspective view, as seen obliquely from the front right-hand side, of a wearable joint driving device according to Embodiment 3 of the present invention; FIG. 10 is a perspective view, as seen obliquely from the front left-hand side, of the wearable joint driving device of FIG. 9; FIG. 11 is a perspective view, as seen obliquely from the rear left-hand side, of the wearable joint driving device of FIG. 9; and FIG. 12 is an exploded perspective view showing the left-arm side frame construction of the wearable joint driving device of FIG. 9. While FIGS. 9 through 11 only show an actuator for driving the left arm for the sake of simplicity, in reality, there is arranged, symmetrically therewith, an actuator for driving the right arm.

In the drawings, a torso frame 31 as a first frame member is put on the torso. The torso frame 31 is provided with a head portion insertion hole 31a through which the head portion is to be passed. Further, the torso frame 31 has a torso frame main body 32 supported by the shoulder, a chest frame 33 rotatably connected to the torso frame main body 32 through the intermediation of a plurality of hinges 34 and abutting the chest portion, and a protrusion 35 protruding upwardly from the back portion of the torso frame main body 32 and facing the neck or the back of the head.

In this way, the torso frame 31 does not entirely cover the upper part of the body but sandwiches solely the chest portion and the upper part of the back between front and rear. The chest frame 33 is rotated relative to the torso frame main body 32 according to the figure of the wearing person.

A shoulder frame 37 as a rotation support member is connected to each shoulder portion of the torso frame main body 32 through the intermediation of a joint portion 36. The shoulder frame 37 has a ring-like shoulder frame main body 38 connected to the joint portion 36, and a ring-like shoulder frame rotating portion 39 rotatably fit-engaged within the shoulder frame main body 38.

The shoulder frame main body 38 is provided with an extension 38a with an arcuate sectional configuration extending outwards. Further, on the inner peripheral surface of the shoulder frame main body 38, there is provided a protrusion 38b (FIG. 12) guiding the rotation of the shoulder frame rotating portion 39.

The shoulder frame rotating portion 39 is provided with a pair of upper arm frame connecting portions 39a. Further, in the outer peripheral surface of the shoulder frame rotating portion 39, there is provided a guide groove 39b (FIG. 12) into which the protrusion 38b is inserted. When the shoulder frame rotating portion 39 is rotated relative to the shoulder frame main body 38, the protrusion 38b makes a relative sliding movement within the guide groove 39b.

A cylindrical upper arm frame 41 as a second frame member is connected to the shoulder frame rotating portion 39 through the intermediation of a pair of upper arm frame connecting belts 40. The upper end portions of the upper arm frame connecting belts 40 are fixed to the upper arm frame connecting portions 39a.

The upper arm frame 41 has a cylindrical upper arm frame main body 42 connected to the upper arm frame connecting belts 40, and a ring-like upper arm frame rotating portion 43 rotatably fit-engaged with the outer peripheral portion of the upper arm frame main body 42.

On the outer peripheral surface of the upper arm frame main body 42, there are provided a pair of protrusions 42a (FIG. 12) guiding the rotation of the upper arm frame rotating portion 43. The upper arm frame rotating portion 43 is provided with a pair of guide slits 43a into which the protrusions 42a are inserted. When the upper arm frame rotating portion 43 is rotated relative to the upper arm frame main body 42, the protrusions 42a make a relative sliding movement within the guide slits 43a.

A cylindrical forearm frame 45 is connected to the upper arm frame rotating portion 43 through the intermediation of a pair of link members 44. Each link member 44 has a first link member 44a connected to the upper arm frame rotating portion 43, and a second link member 44b connected to the forearm frame 45. The first and second link members 44a, 44b are rotatably connected to each other.

The torso frame 31, the shoulder frame 37, the upper arm frame 41, and the forearm frame 45 are formed of a metal, such as aluminum or aluminum alloy.

Between the upper end portion of the protrusion 35 and the forward end portion of the extension 38a, there is provided a first actuator 51 as an auxiliary member actuator for rotating the shoulder frame 37 relative to the torso frame 31. The end portions of the first actuator 51 are respectively fixed to the protrusion 35 and the extension 38a.

Between the chest frame 33 and the forward end portion of the extension 38a, there is provided a second actuator 52 as an auxiliary member actuator for rotating the shoulder frame 37 relative to the torso frame 31. The end portions of the second actuator 52 are respectively fixed to the chest frame 33 and the extension 38a.

Between the back surface of the torso frame main body 32 and the forward end portion of the extension 38a, there is provided a third actuator 53 (shown only in FIG. 11) as an auxiliary member actuator for rotating the shoulder frame 37 relative to the torso frame 31. The end portions of the third actuator 53 are respectively fixed to the torso frame main body 32 and the extension 38a.

Between the back surface of the shoulder frame main body 38 and the front surface of the upper arm frame main body 42, there is provided a fourth actuator 54 for rotating the upper arm frame 41 and the shoulder frame rotating portion 39 relative to the shoulder frame main body 38. The fourth actuator 54 is arranged so as to be wrapped around the outer peripheral surface of the shoulder frame main body 38. Further, the end portions of the fourth actuator 54 are respectively fixed to the shoulder frame main body 38 and the upper arm frame main body 42.

Between the front surface of the shoulder frame 38 and the back surface of the upper arm frame main body 42, there is provided a fifth actuator 55 for rotating the upper arm frame 41 and the shoulder frame rotating portion 39 relative to the shoulder frame main body 38. The fifth actuator 55 is arranged so as to be wrapped around the outer peripheral surface of the shoulder frame main body 38. Further, the end portions of the fifth actuator 55 are respectively fixed to the shoulder frame main body 38 and the upper arm frame main body 42.

The driving forces generated by the fourth and fifth actuators 54, 55 are in opposite directions.

Between the upper end portion of the protrusion 35 and the outer side surface (the side surface of the side opposite to the torso) of the upper arm frame main body 42, there is provided a sixth actuator 56 as a second frame member actuator for rotating the upper arm frame 41 relative to the torso frame 31. The end portions of the sixth actuator 56 are respectively fixed to the protrusion 35 and the upper arm frame main body 42.

Between the upper arm frame main body 42 and the upper arm frame rotating portion 43, there are provided seventh and eighth actuators 57, 58 for rotating the upper arm frame rotating portion 43 and the forearm frame 45 relative to the upper arm frame main body 42. The seventh and eighth actuators 57, 58 are arranged so as to be wrapped around the outer peripheral surface of the upper arm frame 41. The end portions of the seventh and eighth actuators 57, 58 are respectively fixed to the upper arm frame main body 42 and the upper arm frame rotating portion 43.

Further, the driving forces generated by the seventh and eighth actuators 57, 58 are in opposite directions.

Between the first link member 44a and the forward end portion (lower end portion) of the forearm frame 45, there are provided ninth through twelfth actuators 59 through 62 for rotating the forearm frame 45 relative to the upper arm frame 41. The end portions of the ninth through twelfth actuators 59 through 62 are respectively fixed to the first link member 44a and the forearm frame 45.

Between the back surface of the upper arm frame rotating portion 43 and the back surface of the forearm frame 45, there is provided a thirteenth actuator 63 (shown only in FIG. 11) for rotating the forearm frame 45 relative to the upper arm frame 41.

Figure 13:
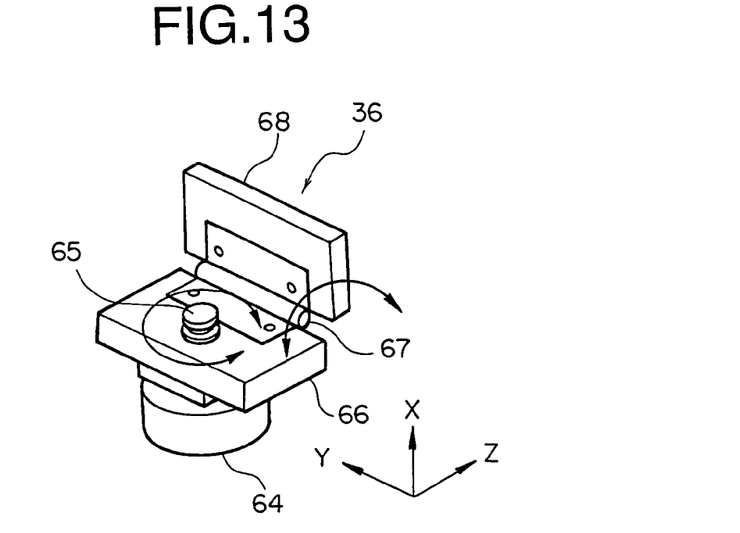
FIG. 13 is a perspective view of a joint portion of FIG. 9.

Next, FIG. 13 is a perspective view of the joint portion 36 of FIG. 9. In the drawing, a base 64 is fixed to the torso frame main body 32. The base 64 is provided with a shaft 65. The axis of the shaft 65 is parallel to the X-axis in the drawing. Further, mounted on the base 64 is a rotation base 66 rotatable by 360 degrees around the shaft 65.

A shoulder frame connecting member 68 is connected to the rotation base 66 through the intermediation of a hinge 67. The shoulder frame connecting member 68 is rotatable by 180 degrees with respect to the rotation base 66. The rotation axis of the shoulder frame connecting member 68 is parallel to the Y-axis in the drawing. The shoulder frame main body 38 is fixed to the shoulder frame connecting member 68.

By connecting the torso frame 31 and the shoulder frame 37 through the intermediation of the joint portion 36, it is possible to move the shoulder frame 37 in a direction in which the upper arm is raised and lowered relative to the torso and in a direction in which the upper arm is moved forwards and backwards.

The basic construction of the first through thirteenth actuators 51 through 63 is the same as that shown in FIGS. 2 and 3.

The control system for the first through thirteenth actuators 51 through 63 is the same as that of Embodiment 1 (FIG. 4).

Further, it is also effective to use a cover covering the outer peripheral portion and the inner peripheral portion of the entire device in order to prevent clothes from being caught by the frames and to prevent the actuators from colliding with peripheral objects to suffer damage, when actually putting on the device. In this case, the cover can be formed, for example, of cloth.

Next, the operation of the device will be described. By supplying air to the sixth actuator 56 in the state as shown in FIGS. 9 through 11, the length of the sixth actuator 56 is reduced, and the upper arm frame 41 is raised. In this state, air is supplied to the first through third actuators 51 through 53, whereby the upper arm frame 41 is further raised together with the shoulder frame 37.

That is, the upper arm frame 41 is rotated from a first position to a second position with respect to the torso frame 31 by the driving force of the sixth actuator 56. By driving the first through third actuators 51 through 53, with the upper arm frame 41 being at the second position, the upper arm frame 41 is rotated together with the shoulder frame 37. This causes the upper arm frame 41 to be rotated to a third position where the angle it makes with the first position is larger than that when it is at the second position.

Further, by supplying air to the second or third actuator 52, 53 in the state of FIGS. 9 through 11, the shoulder frame 37 is rotated around the shaft 65 of the joint portion 36 so as to move the shoulder forwards and backwards.

Further, by supplying air to the fourth or fifth actuator 54, 55, the shoulder frame rotating portion 39 and the upper arm frame 41 are rotated so as to swing the arm forwards and backwards.

Furthermore, by supplying air to the seventh or eighth actuator 57, 58, the upper arm frame rotating portion 43 and the forearm frame 45 are rotated so as to twist the forearm relative to the upper arm.

Further, air is selectively supplied to the ninth through thirteenth actuators 59 through 63, whereby the forearm frame 45 is rotated so as to bend and stretch the forearm relative to the upper arm.

In the wearable joint driving device described above, even when the torso frame 31, the shoulder frame 37, the upper arm frame 41, and the forearm frame 45 have a level of rigidity which allows the same operation irrespective of whether they are on the human body or not, so that generation of wrinkles and looseness in the frames 31, 37, 41, 45 is prevented, and it is possible to achieve an improvement in terms of driving force transmission efficiency and an increase in operating amount and driving force.

Further, due to the use of the shoulder frame 37 and the first and second actuators 51, 52 rotating the shoulder frame 37, it is possible to expand the rotation range for the upper arm frame 41.

Further, the torso frame 31 has the torso frame main body 32 supported by the shoulder portion of the torso, and the chest frame 33 rotatably connected to the torso frame main body 32 and abutting the chest portion of the torso, so that it is possible to facilitate the wearing of the device as a whole regardless of the figure of the wearing person, making it possible to substantially reduce the requisite time for putting on and taking off the device.

Furthermore, the torso frame 31 is provided with the protrusion 35 protruding from the back portion of the torso frame main body 32, and the first and sixth actuators 51, 56 are connected to the protrusion 35, so that the arrangement of the actuators 51, 56 is facilitated, and it is possible to effectively exert the driving force of the actuators 51, 56.

Further, the joint portion 36 has the rotation base 66 rotatable around the shaft 65, and the shoulder frame connecting member 68 rotatably connected to the rotation base 66 through the intermediation of the hinge 67, so that it is possible to achieve an improvement in terms of degree of freedom for the operation of the shoulder frame 37, making it possible to realize various movements.

Further, the shoulder frame 37 is provided with the extension 38a extending outwards, and the first and second actuators 51, 52 are provided between the torso frame 31 and the extension 38a, so that the arrangement of the actuators 51, 52 is facilitated, and the driving force of the actuators 51, 52 can be effectively exerted.

Furthermore, the shoulder frame 37 has the shoulder frame main body 38, and the shoulder frame rotating portion 39 rotatably fit-engaged with the shoulder frame main portion 38, so that the upper arm frame can be rotated so as to move the upper arm forwards and backwards with a simple structure.

Further, the upper arm frame 41 has the upper arm frame main body 42, and the upper arm frame rotating portion 43 rotatably fit-engaged with the upper arm frame main body 42, so that it is possible to rotate the forearm frame so as to twist the forearm relative to the upper arm with a simple structure.

The shoulder frame 37, the upper arm frame 41, and the forearm frame 45 described above can be operated singly or in combination by driving selectively or in parallel predetermined ones of the actuators 51 through 63.

Further, the forearm frame 45 is connected to the upper arm frame 41 through the link bodies with the first and second link members 44a, 44b, so that it is possible to reduce the sizes of the upper arm frame 41 and the forearm frame 45, thereby achieving a reduction in the weight as a whole.

Embodiment 4

Figure 14:
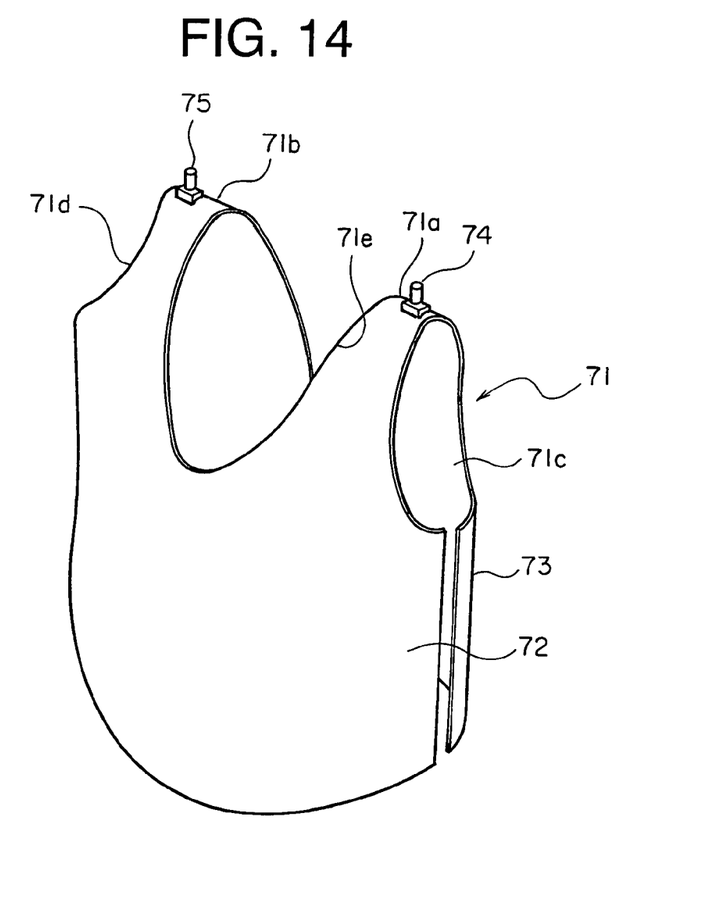
FIG. 14 is a perspective view of a torso frame of a wearable joint driving device according to Embodiment 4 of the present invention.

Next, FIG. 14 is a perspective view of the torso frame of a wearable joint driving device according to Embodiment 4 of the present invention. In the drawing, a torso frame 71 has a front surface portion 72 covering the front surface of the torso, and a back surface portion 73 covering the back surface of the torso. The front surface portion 72 and the back surface portion 73 are rotatably connected to each other at connecting portions 71a, 71b situated on the shoulder portions through the intermediation of hinges (not shown).

Further, the torso frame 71 is provided with sleeve openings 71c, 71d through which the arms are to be passed, and a neck opening 71e through which the neck is to be passed.

Fixed to the shoulder portions of the torso frame 71 are shoulder frame mounting portions 74, 75 for the mounting of the shoulder frame 37 as shown, for example, in Embodiment 3.

When putting on the wearable joint driving device using the torso frame 71 of Embodiment 4, the front surface portion 72 and the back surface portion 73 are first opened, and the arms are passed through the sleeve openings 71c, 71d, thus the torso frame 71 is attached to the torso. Thereafter, the shoulder frame 37 is mounted to the shoulder frame mounting portions 72, 73.

At this time, the upper arm frame 41 and the forearm frame 45 as shown in Embodiment 3 are previously connected to the shoulder frame 37 to be assembled as an arm attachment unit. Further, the actuators 51 through 63 are also previously mounted to the arm attachment unit.

Thus, the mounting of the shoulder frame 37 to the shoulder frame mounting portions 72, 73 is effected after the arms have been passed through the arm attachment unit. Thereafter, the actuators 51, 52, 56 are connected to the torso frame 71.

In this way, it is also possible to make the torso frame 71 and the arm attachment unit detachable to each other, attaching them separately.

As described above, when worn by a person physically handicapped, the wearable joint driving device of the present invention can assist the person in his or her action. Further, when worn by a person in normal health, it generates a force exceeding the muscular power of the wearing person to assist him or her in operation. As a result, it is possible to mitigate the physical burden on a person performing nursing/assistance, for example. That is, it is possible even for an aged person or a woman to perform a heavy work, such as taking up somebody in his or her arms. Further, regardless of whether a person is in normal health or physically handicapped, it is possible to assist him or her in performing physical work, maintain his or her posture, assist posture maintenance, or amplify his or her force.

Further, when attached to a robot, the wearable joint driving device of the present invention can be used as a robot drive source.

Furthermore, by forming the frame members of a material allowing transmittance of X-rays, for example, the device can be used in an X-ray inspection with an external force applied. Further, it can also be used in an MRI inspection and a CT inspection.

The invention claimed is:

1. A wearable joint driving device comprising:
    a main frame attachable to a main part of a human body to surround the main part;
    a cylindrical rotatable frame connected to the main frame through a rotation mechanism to be rotatable in a bending direction of a joint portion of the human body, the rotatable frame being formed by a material having a predetermined rigidity;
    at least one fluid pressure actuator having an expansion/contraction member undergoing expansion/contraction through supply/discharge of a fluid and a covering net covering an outer periphery of the expansion/contraction member, end portions of the fluid pressure type actuator being connected to the main frame and the rotatable frame, the expansion/contraction member being reduced in length through expansion to thereby generate a driving force; and
    a control unit for controlling supply and discharge of the fluid to and from the fluid pressure actuator.

2. The wearable joint driving device according to claim 1, wherein:
    the main frame includes a torso frame attachable to the torso of the human body and a shoulder frame rotatably connected to the torso frame, and
    the rotatable frame includes an upper arm frame rotatably connected to the shoulder frame.

3. The wearable joint driving device according to claim 2, wherein the torso frame includes a torso frame main body supported by a shoulder portion and a back portion of the torso, and a chest frame connected to the torso frame main body to be capable of opening and closing and in contact with a chest portion of the torso.

4. The wearable joint driving device according to claim 3, wherein:
    a shoulder frame rotation mechanism for rotating the shoulder frame relative to the torso frame is provided between the torso frame main body and the shoulder frame, and
    the fluid pressure type actuators are further connected between a back portion of the torso frame and the shoulder frame and between the chest frame and the shoulder frame.

5. The wearable joint driving device according to claim 4, wherein the shoulder frame rotation mechanism has:
    a shaft provided at a shoulder portion of the torso frame;
    a first rotating member rotatably provided at the shaft; and
    a shoulder frame supporting member connected to the first rotating member for rotating the shoulder frame in a plane intersecting a rotating plane of the first rotating member.

6. The wearable joint driving device according to claim 2, wherein:
    the rotatable frame further includes a cylindrical forearm frame rotatably connected to a tip portion of the upper arm frame, and
    the fluid pressure type actuator is further connected between the upper arm frame and the forearm frame.

7. The wearable joint driving device according to claim 6, wherein a forearm frame rotation mechanism and the fluid pressure type actuators for bending, stretching and twisting the forearm frame relative to the upper arm frame are provided between the upper arm frame and the forearm frame.

8. The wearable joint driving device according to claim 7, wherein the forearm frame rotation mechanism has:
- a first ring member rotatably fit-engaged with the upper arm frame; and
- a pair of link bodies for rotatably connecting the first ring member with the forearm frame.

9. The wearable joint driving device according to claim 8, wherein each link body has a first link member connected to the first ring member and a second link member connected to the forearm frame, the first and second link members being rotatably connected to each other.

10. The wearable joint driving device according to claim 7, wherein the fluid pressure type actuator for twisting the forearm frame relative to the upper arm frame is arranged so as to be wrapped around the upper arm frame and the first ring member.

11. The wearable joint driving device according to claim 2, wherein:
- an upper arm frame rotation mechanism for rotating the upper arm frame relative to the shoulder frame in the up and down direction and the back and forth direction is provided between the shoulder frame and the upper arm frame; and
- the fluid pressure type actuators are connected between the torso frame and the upper arm frame and between the shoulder frame and the upper arm frame.

12. The wearable joint driving device according to claim 11, wherein the upper arm frame rotation mechanism has:
- a second ring member rotatably fit-engaged with the cylindrical shoulder frame; and
- a pair of belts for rotatably connecting the second ring member with the upper arm frame.

13. The wearable joint driving device according to claim 11, wherein the fluid pressure type actuator for rotating the upper arm frame in the back and forth direction is arranged between the shoulder frame and the second ring member so as to be wrapped around the shoulder frame and the second ring member.

14. The wearable joint driving device according to claim 2, wherein:
- a protrusion is provided at a back portion of the torso frame; and
- the fluid pressure type actuator is connected between the protrusion and the upper frame.

15. A wearable joint driving device worn by a driven body having first and second wearing members and a joint portion rotatably connecting the first and second wearing members to drive the joint portion, the wearable joint driving device comprising:
- a first frame member to be attached to the first wearing member;
- a second frame member to be attached to the second wearing member;
- a rotation support member rotatably connected to the first frame member;
- a second frame member actuator provided between at least one of the first frame member and the rotation support member and the second frame member and adapted to rotate the second frame member with respect to the first frame member; and
- a support member actuator provided between the first frame member and the rotation support member and adapted to rotate the rotation support member with respect to the first frame member, wherein the second frame member actuator and the support member actuator are fluid pressure type actuators respectively having an expansion/contraction member undergoing expansion/contraction through supply/discharge of a fluid and a net member covering an outer periphery of the expansion/contraction member, the expansion/contraction member being reduced in length through expansion to generate a driving force, wherein the second frame member is rotated from a first position to a second position by the driving force of the second frame member actuator, and wherein, by driving the support member actuator with the second frame member being at the second position, the second frame member is rotated together with the rotation support member, whereby the second frame member is rotated to a third position where the angle the second frame member makes with the first position is larger than that when the second frame member is at the second position.

16. The wearable joint driving device according to claim 15, wherein the first wearing member is a torso, the second wearing member is an upper arm, and the joint portion is a shoulder joint portion, wherein the first frame member is a torso frame to be attached to the torso, the second frame member is an upper arm frame to be attached to the upper arm, and the rotation support member is a shoulder frame rotatably connected to the torso frame.

* * * * *